US005713352A

United States Patent [19]
Essenpreis et al.

[11] Patent Number: 5,713,352
[45] Date of Patent: Feb. 3, 1998

[54] METHOD FOR INVESTIGATING A SCATTERING MEDIUM WITH INTENSITY-MODULATED LIGHT

[75] Inventors: Matthias Essenpreis, Gauting; Hans-Peter Haar, Wiesloch; Dirk Boecker, Heidelberg; Alexander Knuettel, Weinheim, all of Germany

[73] Assignee: Boehringer Mannheim GmbH, Mannheim, Germany

[21] Appl. No.: 572,641

[22] Filed: Dec. 14, 1995

[30] Foreign Application Priority Data

Dec. 21, 1994 [DE] Germany ............... 44 45 683.2

[51] Int. Cl.$^6$ ..................................................... A61B 5/00
[52] U.S. Cl. ........................ 128/633; 128/664; 128/665
[58] Field of Search ........................... 128/633, 664, 128/665

[56] References Cited

U.S. PATENT DOCUMENTS

| | | |
|---|---|---|
| 4,972,331 | 11/1990 | Chance . |
| 5,057,695 | 10/1991 | Hirao et al. . |
| 5,119,815 | 6/1992 | Chance . |
| 5,122,974 | 6/1992 | Chance . |
| 5,167,230 | 12/1992 | Chance . |
| 5,285,783 | 2/1994 | Secker . |
| 5,309,907 | 5/1994 | Fang et al. ................... 128/633 |

FOREIGN PATENT DOCUMENTS

| | | |
|---|---|---|
| 1 962 335 | 3/1972 | Germany . |
| 42 09 886 A1 | 10/1992 | Germany . |
| 42 42 232 A1 | 6/1994 | Germany . |
| 43 41 063 A1 | 6/1994 | Germany . |
| 43 14 835 A1 | 11/1994 | Germany . |
| 43 18 823 A1 | 12/1994 | Germany . |
| WO 93/09423 | 5/1993 | WIPO . |

OTHER PUBLICATIONS

"Electro-Optical Simulator for Pulse Oximeters", *Medical & Biological Engineering & Computing*, Zhou et al, Sep. 1993, pp. 534-539.

"Time-Resolved Spectroscopy of Hemoglobin and Myoglobin in Resting and Ischemic Muscle", *Analytical Biochemistry*, 174, Chance et al, 1988, pp. 698-707.

"Gigahertz Frequency-Domain Fluorometry: Resolution of Complex Intensity Decays, Picosecond Processes and Future Developments", Department of Biological Chemistry, University of Maryland, Lakowicz, pp. 169-186.

"A multiwavelength, Wideband, Intensity Modulated Optical Spectrometer for Near Infrared Spectroscopy and Imaging", Duncan et al, *SPIE*, vol. 1888, pp. 248-257.

*Primary Examiner*—Jennifer Bahr
*Assistant Examiner*—Eric F. Winakur
*Attorney, Agent, or Firm*—Nikaido, Marmelstein, Murray & Oram LLP

[57] ABSTRACT

The invention concerns a method for investigating a scattering medium, especially a biological matrix, with intensity-modulated light. In order, in such a frequency-domain measuring procedure, to reduce the expenditure on electronics without restricting accuracy of measurement, a method is proposed, in which, in order to investigate a scattering medium, especially a biological matrix, with intensity-modulated light, a high-frequency modulation signal is generated by a frequency generator (18), the intensity of a light emitter (10) is modulated with a modulation signal and the light from the light emitter (10) is radiated into the medium, the modulation signal includes frequency chirps during which the modulation frequency is tuned from an initial frequency to a final frequency, the modulation signal is delivered from the frequency generator (18) via at least two different signal paths (23A, 24) to a signal mixer (31), so that during a frequency chirp the input signals of the signal mixer (31) differ by a differential frequency whose magnitude is a function of the difference between the signal transit times over the at least two signal paths (23A, 24) and of the rate of change of the modulation frequency, wherein at least one of the signal paths includes a light path section (20A) passing through the medium as a measurement signal path (23A), and the output signal of the signal mixer (31) is further processed to produce information relating to the scattering medium (FIG. 2).

17 Claims, 3 Drawing Sheets

METHOD FOR INVESTIGATING A SCATTERING MEDIUM WITH INTENSITY-MODULATED LIGHT

The invention concerns a method for investigating a scattering medium, especially a biological matrix, with intensity-modulated light.

In such a process, light is radiated into the medium as primary light at an irradiation site, and light emerging from the scattering medium is detected as secondary light at a detection site located at a defined measurement distance from the irradiation site, i.e. it is converted into an electrical measurement signal by a photoelectric converter acting as a light receiver. By comparing the irradiated primary light and the detected secondary light, a measurement quantity is determined whose measured value is a function of the interaction between the light and the scattering medium, thereby representing a measure of the required result of the investigation. Such a measurement quantity is often referred to as the "quantifiable parameter" characteristic of the investigation result.

The invention relates to cases where multiple scattering of the light takes place between the irradiation site and the detection site. This means that the scatter centers in the scattering medium are so dense that the mean free path of photons in the medium is far shorter than the light path between irradiation site and detection site, so that the light is scattered many times on its path between the two sites (at least 10, preferably at least 100 times).

One particularly important application of the invention is the investigation of a biological matrix. In this context a "biological matrix" is a body fluid (especially blood) or tissue of a living organism. Both in the biological tissue, especially skin tissue, and in typical body fluids, so many scatter centers are present that multiple scattering takes place, even with a short measurement distance.

In this context, analytical methods are of particular importance in which the concentration of an analyzed substance is determined, and the parameter represents a measurement quantity which is required to determine the desired concentration. Such analytical methods are of great medical importance, since they enable concentrations of particular analyzed substances to be determined directly in the tissue, i.e. "in vivo", without taking a blood sample. In the following, without limiting the generality, reference is made to biological matrices, especially tissues, as an example of a scattering medium in the sense used in the invention.

As a general rule the light wavelengths considered in particular for measurements on biological matrices are between approximately 300 nm and several thousand nm, i.e. in the spectral range between near UV and infrared light. The expression "light" must not be construed as being restricted to the visible light spectrum.

The invention relates in particular to processes in which the primary light is not radiated into the scattering medium with a constant intensity, but in which it is amplitude-modulated with a modulation signal whose frequency is usually in the radio-frequency range above 100 MHz. Light-intensity waves are thereby propagated in the biological matrix, the wavelengths of which are equivalent to the quotient of the phase velocity of the light-intensity wave in the biological matrix and the modulation frequency.

Such methods are referred to as "frequency domain measurements". The frequency domain measuring method ("FD method" in the following) enables two types of parameter ("FD parameters") to be determined.

Firstly the AC amplitude and/or the DC amplitude of the detected secondary light can be determined in relation to the irradiated primary light. These two parameters describe the change in the intensity of the light due to interaction with the biological matrix and are consequently collectively referred to as "intensity parameters".

Secondly it is possible to determine the phase shift of the light in the medium. Said phase shift is the result of the transit time of the light between the irradiation site and the detection site in the biological matrix. The transit time dt is directly linearly related to the phase shift dF (dt=dF/W, where W is the modulation frequency of the primary light). The phase shift is thus a transit-time parameter. Generally speaking, in the context of this invention, a transit-time parameter can be any quantifiable parameter of the light that is correlated with the transit time, i.e. represents a clear measure of the transit time of the light between irradiation site and detection site in the scattering medium.

As already mentioned, the parameters are determined in each instance from the detected secondary light in relation to the irradiated primary light. In the following the abbreviations AC, DC and P are used for the three parameters referred to above: AC amplitude, DC amplitude and phase shift.

Use of FD methods to determine a parameter of the light as a measurement quantity for the analytical determination of the concentration of an analyzed substance in a biological matrix has hitherto been discussed principally in connection with time-resolved spectroscopy (FD spectroscopy). This aims to overcome a basic problem of the spectroscopy of scattering media, namely lack of knowledge of the optical path length. This knowledge is required to quantify the absorption spectra measured by spectroscopic methods and to compute the concentration of an absorbing substance. In a non-scattering medium, the optical path length is the length of the optical cell. In a scattering medium there is a statistical distribution of path lengths due to the large number of scattering processes. Using FD spectroscopy, it is possible to measure the randomly distributed mean optical path in the scattering medium and to associate it with the particular absorption value.

Such methods are known, for example, from the following publications.

J. R. Lackowicz: "Gigahertz Frequency-Domain Fluorometry: Resolution of Complex Intensity Decays, Picosecond Processes and Future Developments" Photon Migration in Tissues, Academic Press/New York, Edited by Britton Chance, pp. 169–186, 1989.

B. Chance et al.: "Time-resolved spectroscopy of hemoglobin ... ", Analytical Biochemistry, 174 (1988) p. 698 to 707.

U.S. Pat. Nos. 4,972,331—5,119,815—5,122,974—5,167,230.

A. Duncan et al.: "A multiwavelength, wide band, intensity modulated optical spectrometer for near infrared spectroscopy and imaging", Proc. SPIE 1888 (1993), 248–257.

The examples given in these publications relate to the analysis of highly absorbent substances with pigment properties, especially the red blood pigment hemoglobin.

In international patent application PCT/DE 94/01290 filed earlier, but not previously published, a method for determining the concentration of glucose in a biological matrix is described, in which, using an FD measuring method, a transit-time parameter of the light inside the biological matrix is measured as a measurement quantity correlating with the glucose concentration. The principle on which the analysis is based differs fundamentally from the spectroscopic analyses discussed above. The optical absorption of glucose is in the applicable wavelength range so small that it cannot be used for practical analysis. Rather the analysis here is based on the fact that the mean optical path length of photons inside the heterogeneous biological matrix is affected by the glucose concentration to a surprisingly great extent. The mean optical path length is consequently a direct measure of the glucose concentration. Measurement at several different wavelengths, as is customary for spectroscopic measurements, are not required with this principle.

Information about the FD parameters can also be used for imaging processes, for example for breast examinations for tumors. This requires to scan the investigated volume by the primary light, i.e. a scan of the respective partial area of the surface of the tissue is required. The information concerning phase shift and intensity obtained in this way from the secondary light can be further processed into image information, as described in the publication by M. Kaschke et al.: "Transillumination Imaging of Tissue by Phase Modulation Techniques", OEA Proceedings on Advances in Optical Imaging and Photon Migration, 21 (1994), 88–92.

In known FD procedures, the heterodyne measuring method has in most cases been used to measure the phase shift. In addition to the modulation frequency f1 with which the primary light is modulated, a second constant frequency f2 is generated, differing from f1 by a relatively small differential frequency df. The measurement signal of the light receiver, modulated with the frequency f1, is mixed with frequency f2 in an electronic signal-mixer, and the output signal from the mixer is measured by a narrow-band frequency-selective measuring principle, for example a lock-in amplifier, tuned to the differential frequency df (also referred to as the "cross-correlation frequency").

To implement this principle two high-frequency generators (over 100 MHz) for the frequencies f1 and f2 are required. The stability of the oscillators must meet strict requirements in order to avoid disturbing fluctuations of the cross-correlation frequency (which is approximately 100 Hz to 50 kHz). This calls for a considerable expense on electronics.

On this basis the invention is concerned with the problem of providing a method for investigating biological matrices and other similarly scattering media, employing the FD system, with which the electronic outlay is reduced compared with known methods, but without restricting the accuracy of measurement.

The problem is solved by a method for investigating a scattering medium, especially a biological matrix, with intensity-modulated light, in which a high-frequency modulation signal is generated by a frequency generator, the intensity of a light emitter is modulated with the modulation signal, and the light emitted by the light emitter is radiated into the medium, the modulation signal includes frequency chirps, during which the modulation frequency is tuned from an initial frequency to a final frequency, the modulation signal is delivered from the frequency generator to a signal mixer over at least two different signal paths, so that, during a frequency chirp, the input signals of the signal mixer differ by a differential frequency the amount of which is a function of the difference between the signal transit times over the at least two signal paths and of the rate of change of the modulation frequency, wherein at least one of the signal paths, as a measurement signal path, includes a light path section passing through the medium, and the output signal of the signal mixer is further processed to provide information relating to the scattering medium.

As a general rule, the signal transit times required for the at least two different signal paths are different, so that the resultant differential frequency is not equal to zero. Within the scope of the invention, embodiments are however also possible in which operational states with the same signal transit times (zero resultant differential frequency) occur on the at least two different signal paths.

Using a method according to the invention, it is possible to measure an FD parameter, especially as a measurement quantity for in-vivo analysis on human tissue, with only one frequency generator, which does not even have to meet special requirements concerning frequency stability. A considerable saving in respect of electronic outlay is thereby achieved without affecting the accuracy of measurement. This is particularly important in applications in which—as for example in the continuous monitoring of the blood glucose level of diabetics—analysis should be possible using small inexpensive equipment which can be made available to the individual user.

The invention is explained in more detail in the following by reference to the embodiments represented diagrammatically in the Figures.

Figure 1:
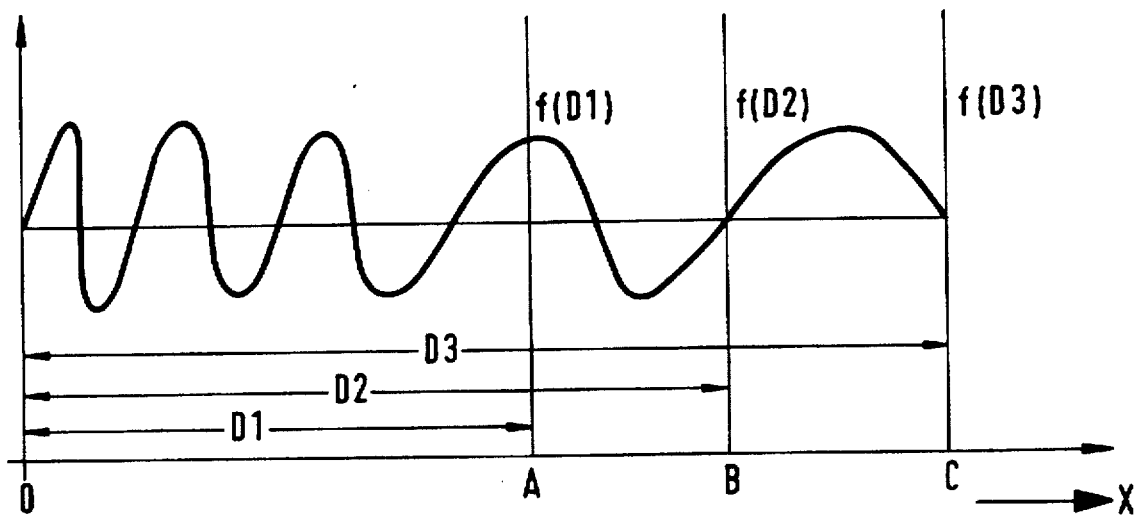
FIG. 1 shows a diagram to explain the invention.

FIG. 1 illustrates diagrammatically the one-dimensional propagation behaviour of light along an X axis. The light is emitted by a light source arranged at location 0 and modulated with a steadily rising modulation frequency. If the modulation frequency rises monotonically during a frequency chirp, at any instant within the chirp different frequencies are measured at different detection sites (A, B, C) along the propagation direction (X axis). FIG. 1 represents an "instantaneous recording". While in the vicinity of the 0 point (i.e. the location of the light source) a high modulation frequency is measured (indicated by a short wavelength), at greater distances the modulation frequency decreases continuously because the light detectable there was emitted at an earlier point of time, i.e. in the chirp with a lower frequency. Of course all the frequencies of a chirp occur at each detection site, but at each particular instant different frequencies are measured at detection sites located at different distances. Consequently, within a frequency chirp with rising frequency at any instant the frequency measured at a detection site A with a shorter measurement distance D1 will be higher than the frequency measured at a detection site B with a greater measurement distance D2.

A frequency chirp in which the frequency varies linearly, or in other words the rate of change (rising or falling) is constant with respect to time is easiest to produce. On this assumption, which is preferred within the scope of the invention, the frequency difference (differential frequency) between two detection sites at different distances from the irradiation site within a frequency chirp is constant with respect to time and proportional to the distance between the detection sites. The following formula thus applies:

$$df = f(D2) - f(D1) = df/dt \cdot (D2-D1) \cdot 1/v \tag{1}$$

df is the differential frequency between two detection sites positioned at measurement distances D1 and D2 from the irradiation site. df/dt is the rate of change of the frequency within the chirp and v is the propagation speed of the light in the medium (obtained from the speed of light c and the index of refraction N, according to $v=c/N$).

The above considerations can be easily generalized: For any arrangement in which a signal is conveyed along two different signal paths with different signal transit times $t_1$ and $t_2$, the differential frequency df is a function of the transit-time difference dt and the rate of change of the modulation frequency in the chirp:

$$df=f(df/dt,dt) \qquad (2)$$

Figure 2:
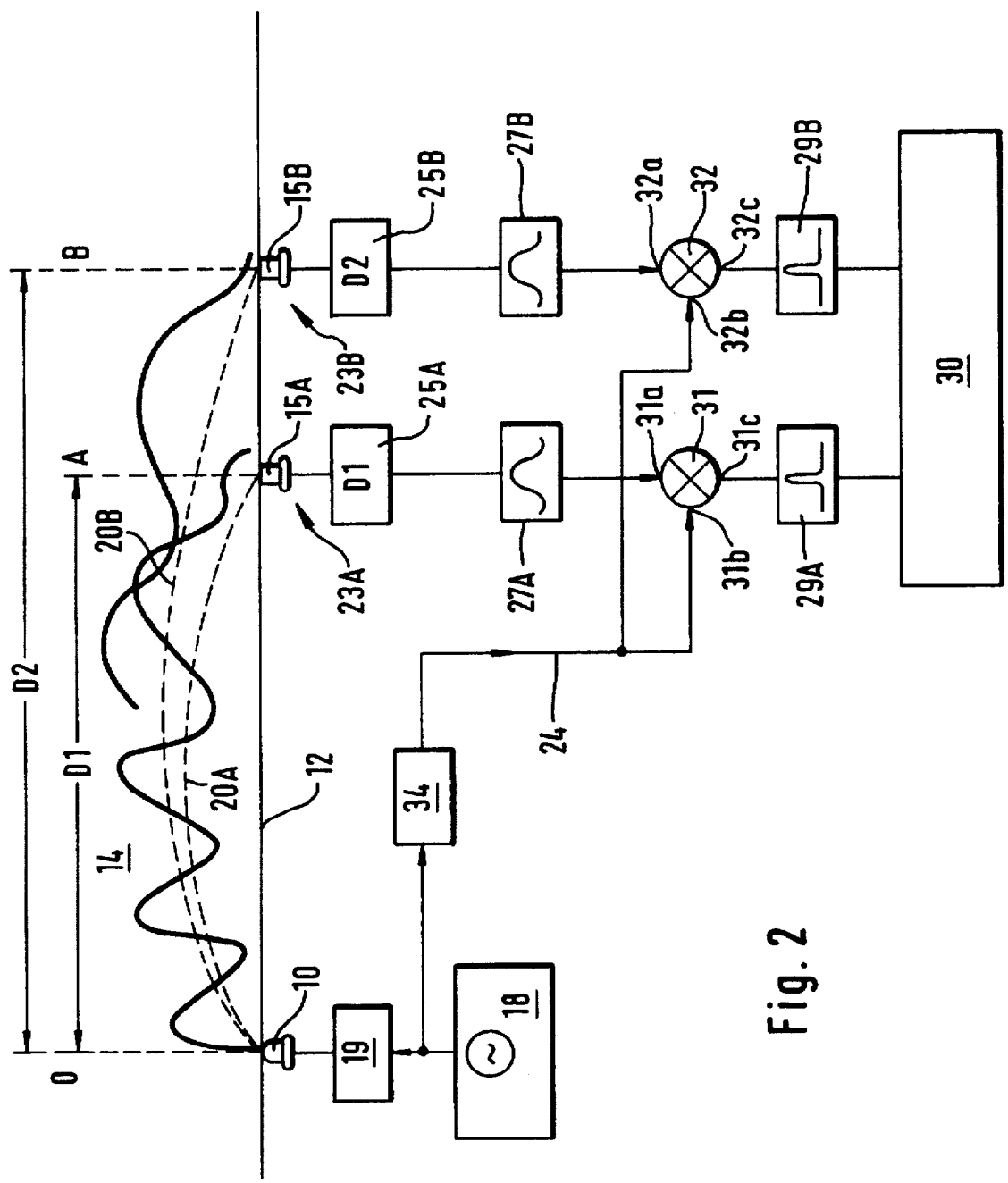
FIG. 2 shows a block diagram of a first arrangement to implement the invention.

FIG. 2 shows a first possibility for implementing the invention. A light emitter 10, for example a light-emitting diode, radiates primary light through a boundary surface 12 into a biological matrix 14 at an irradiation site 0. The biological matrix 14 is preferably skin tissue, and the boundary surface 12 is formed by the surface of the skin. The light emerging from the biological matrix 14 is detected at two detection sites A and B, which are arranged at different measurement distances D1 and D2 from the irradiation site 0.

Photoelectric converters, such as for example photomultipliers or photodiodes, especially avalanche photodiodes, can be used as detectors 15A and 15B. The arrangement and execution of the optical elements are conventional. In this regard, reference can be made for example to the publications mentioned in the introduction. In particular, light emitters and detectors can be arranged either directly against the boundary surface 12, or optical fibers can be used for connection to more remote light-optical elements.

The light emitter 10 is supplied by means of a frequency generator 18 and an amplifier circuit 19 with a supply voltage that is modulated according to the frequency of the frequency generator 18. The modulation signal generated by the frequency generator 18 consists of frequency chirps in the radio-frequency range (RF chirps), within which the modulation frequency rises or falls with a constant rate of change (ramp shape). The bandwidth of a frequency chirp (i.e. the difference between initial frequency and final frequency) should be at least 10 MHz and a maximum of 300 MHz. Overall, modulation frequencies in a very wide window of the frequency spectrum can be used. The modulation frequency should preferably lie within the limits 50 MHz (as the lowest frequency) and 1000 MHz (as the highest frequency).

The light radiated into the biological matrix 14 reaches the different detection sites A and B via symbolically represented light paths. The section of the signal path from the entry of the light at entry site 0 to its emergence at exit sites A and B is denoted as light path section 20A, 20B passing through the medium (hereinafter also abbreviated to "measurement light path section"). The difference between the signal transit times of light travelling the measurement light path sections 20A, 20B corresponds to the distances D1, D2 of the measurement sites from the irradiation site 0. The light emerging at the detection sites A, B is converted into electrical signals by detectors 15A, 15B, amplified in amplifiers 25A, 25B and filtered in relatively broad-band bandpass filters 27A, 27B. The passband of the bandpass filters is tuned to the bandwidth of the frequency chirp, i.e. they block below the lowest frequency and above the highest frequency of the frequency chirp.

The signals are then delivered respectively to a first input 31a, 32a of a first signal mixer 31 and of a second signal mixer 32. The signal paths of the modulation signal from the frequency generator 18 to the light emitter 10, from there via the measurement light path sections 20A, 20B to the detectors 15A, 15B and thence to the inputs 31a, 31b of the signal mixers 31, 32, are denoted overall as measurement signal paths 23A, 23B.

In each case a reference signal is applied to the second input 31b, 32b of the mixers 31, 32 which is delivered to the mixers 31, 32 via a reference signal path 24 from the frequency generator 18. In the context of the present invention a reference signal path is always a signal path which leads from the same frequency generator to the same mixer as a measurement signal path, but does not include a light path section passing through the medium.

The output signals of the mixers 31, 32 at the outputs 31c and 32c are delivered via narrow-band bandpass filters 29A and 29B to a measurement and evaluation unit 30.

Signal transmission via the electrical signal path sections of the measurement signal paths 23A, 23B between the frequency generator 18 and the light emitter 10 and between the receivers 15A, 15B and the mixers 31, 32 is almost free from delay. On the other hand the light in the measurement light path sections 20A, 20B is propagated considerably more slowly because of the higher index of refraction and especially because of the scatter. For an effective propagation speed of $c/10=3\times10^{10}$ mm/s, the resultant delay is $3\times10^{-10}$ seconds per 10 mm distance between the irradiation site and the detection site. With a rate of change of the frequency within the frequency chirp of df/dt=100 MHz/ms this is equivalent to a frequency shift of approximately 30 Hz. Accordingly the differential frequency between the signals detected at measurement sites A and B is 30 Hz when the measurement distances D1 and D2 differ by 10 mm.

In the invention there are at least two different signal paths connecting the same frequency generator to two inputs of a signal mixer. The difference between the signal transit times, in conjunction with the change in the modulation frequency within the frequency chirp, results in a differential frequency between the inputs of the signal mixer, the magnitude of which is a function of the rate of change df/dt and of the difference between the signal transit times. In the embodiment shown in FIG. 2 there are two measurement signal paths 23A and 23B with different measurement light path sections 20A, 20B and a reference signal path 24 without a measurement light path section. Each of these signal paths has a different signal transit time. To each of the inputs 31a, 31b, 32a, 32b of the frequency mixers 31, 32 a measurement signal transmitted via a measurement signal path or a reference signal transmitted via the reference signal path is applied.

The differential frequency at the inputs of the signal mixer, which is caused by the frequency chirp in conjunction with the signal delay, can be used for the downward conversion of the high-frequency input signals to a conveniently measurable differential frequency, which should preferably be between approximately 1 kHz and 30 kHz. The differential frequency obtained with a technically achievable rate of change and with relatively small measurement distances is—as the above calculated example shows—considerably lower.

In the embodiment according to FIG. 2 a delay section 34 is therefore provided in the reference signal path 24. The transit-time difference between the measurement signals transmitted via the measurement signal paths 23A, 23B to the first inputs 31a, 32a of the mixers 31, 32 and the reference signal transmitted via the reference signal path 24 to the second inputs 31b, 32b of the mixers 31, 32 is thereby increased to such an extent that the resultant differential frequency allows a convenient evaluation of the cross-correlation signal resulting from the mixing, using common frequency-selective amplification techniques. In order to ensure a differential frequency of the order of 1 kHz and with a rate of change of the frequency chirp of df/dt=100 MHz/ms the delay time must be approximately 10 ns. Such a delay time can be achieved with high constancy by means of an acousto-optic delay section, wherein the speed of sound, which is far lower compared with the speed of light, allows a compact construction with a path length of approximately 1 mm.

As a result of this measure the input signals at the inputs 31a, 31b and 32a, 32b of the mixers 31, 32 differ by a differential frequency of for example 1 kHz. As with the conventional heterodyne measuring technique, the signal mixing produces a downward conversion of the high-frequency signals in the mixers 31, 32. The FD parameters can consequently be conveniently measured at a suitable relatively low frequency. The narrow-band bandpass filters 29A, 29B suppress DC components and the summation signals from the mixing process. In the measurement and evaluation unit 30 the phase relation and the intensity parameters DC and AC can be determined by known measuring methods, such as are also sometimes used in heterodyne measuring systems. In particular a DSP (digital signal processor), which produces an averaged digitized representation of the mixer output signal via a multiplicity of frequency chirps, is suitable. Its parameters P, AC, DC and also the frequency can be calculated with common algorithms implemented in commercially available measuring instruments of this type.

Since, in the present invention, the modulation frequency varies continuously within a frequency chirp, the phase shift (for a given constant measurement signal path) is also not constant. In fact the phase difference within the frequency chirp increases continuously with rising frequency and decreases continuously with decreasing frequency. In order to measure the phase shift P in a reproducible manner, it is therefore necessary within a frequency chirp to determine the phase at a particular defined instant and to compare the measured values thus obtained. Generally it is simpler to use a differential measurement principle, in which the phase is measured at two defined instants within the frequency chirp, especially at the beginning and end of the frequency chirp, and the difference between these measured values is further processed.

As explained, the delay section 34 is required in order to achieve a cross-correlation frequency that can conveniently be measured with the currently achievable rates of change of the frequency chirp and with the short measurement distances preferred for measurements on biological matrices. With large measurement distances, such as are considered for the investigation of brain tissue or for measurements on technical investigation media, it may also be possible however to achieve a sufficiently high differential frequency at the mixer inputs without a delay section.

Under such measurement conditions it may also be possible to use the differential frequency itself as a transit-time parameter, instead of the phase shift P. This is not possible with short measurement distances because, for example, the resultant differential frequency of 30 Hz in the above calculated example (equivalent to a cycle period of approximately 30 ms) cannot be measured within a frequency chirp of for example 1 ms duration. If, however, by increasing the measurement distance and/or increasing the duration of a frequency chirp and/or increasing the rate of change df/dt, a differential frequency is achieved whose corresponding cycle period is shorter than the duration of the frequency chirp, the measured differential frequency constitutes a direct measure of the transit-time difference between the signal paths.

Insofar as a constant delay section 34 is required to adapt the differential frequency, this can be optionally arranged in one of the two signal paths leading to the same signal mixer.

Figure 3:
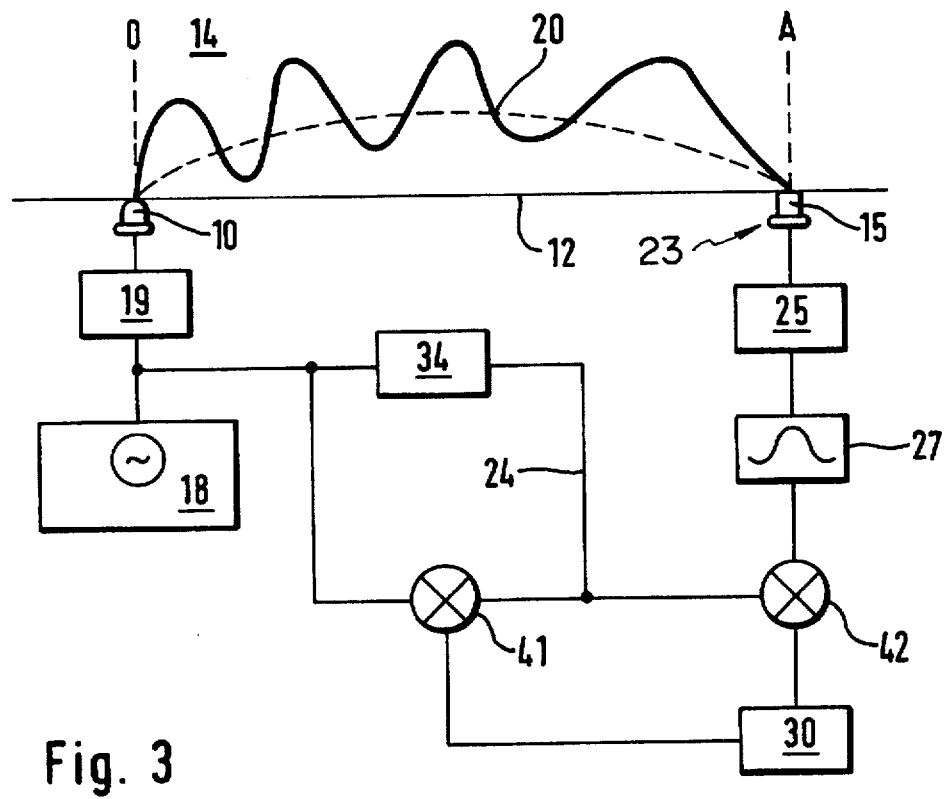
FIG. 3 shows a block diagram of a second arrangement to implement the invention.

FIG. 3 shows that, within the scope of the invention, it is also possible to work with only one light path section 20 passing through the medium. There is a delay section 34 in the reference signal path 24, wherein the signals before and after the delay section 34 are delivered to a signal mixer 41 whose output signal forms the reference frequency for a frequency-selective measurement using the measurement and evaluation unit 30.

As in FIG. 2, the measurement signal path 23 runs from the frequency generator 18 via an amplifier 19 to the light emitter 10 from there via the measurement light path section 20 to the detector 15 and then to the input of signal mixer 42. The light arriving at detector 15 via the light path section 20 passing through the biological matrix 14 is amplified by an amplifier 25 and, after filtering by the filter 27, arrives at a signal mixer 42, to the other input of which the reference signal is applied. Its output signal is delivered to the measurement and evaluation unit 30.

In this embodiment a reference signal for the measurement and evaluation unit 30 and for the downward conversion of the high-frequency measurement signal is produced in a simple manner by the frequency chirp in conjunction with the delay section 34 and the mixer 41. Otherwise the measuring procedure corresponds largely to the previously known heterodyne method.

Figure 4:
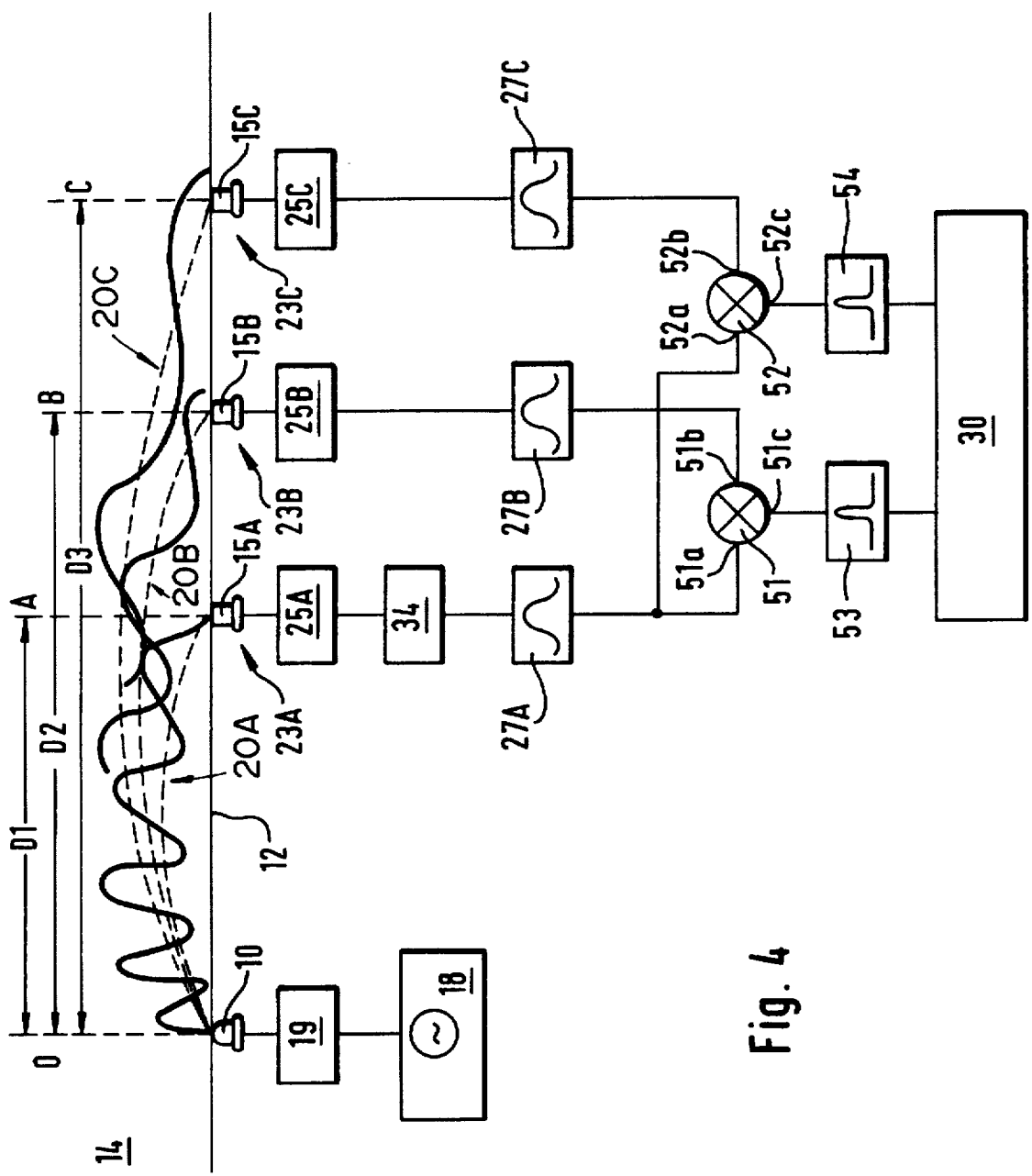
FIG. 4 shows a block diagram of a third arrangement to implement the invention.

FIG. 4 shows an embodiment without a reference signal path. Here at least two and preferably (as shown) at least three detectors 15A, 15B, 15C are provided, by which the secondary light is detected at measurement sites A, B, C located at different measurement distances D1, D2, D3 from the irradiation site 0. As in FIG. 2, irradiation takes place using a frequency generator 18, an amplifier 19 and a light emitter 10. The signal processing on the secondary side of the measurement signal paths also takes place similarly to FIG. 2, using amplifiers 25A, 25B, 25C and filters 27A, 27B, 27C.

In this case too, the modulation signal of the frequency generator 18 is delivered via different signal paths with different signal transit times to at least one signal mixer (with two measurement signal paths) and in the preferred case illustrated to two signal mixers 51, 52. In contrast to FIG. 2, however, all the signal paths 23A, 23B, 23C have a measurement light path section 20A, 20B, 20C passing through the biological matrix 14. One of these measurement signal paths 23A is provided with a delay section 34. The measurement signal of this measurement signal path is delivered in parallel in each case to one input 51a, 52a of the signal mixers 51, 52. The measurement signals of the other two measurement signal paths 23B, 23C are applied to the other input 51b, 52b. The downward-converted cross-correlation signals at the outputs 51c, 52c of the mixers 51, 52 are in turn delivered via narrow-band bandpass filters 53, 54 to the measurement and evaluation unit 30.

As in the embodiment according to FIG. 2, in the embodiments according to FIGS. 3 and 4 the characteristic of the output signal of mixers 31, 32, 42 is determined by known measuring methods, and the phase relation P and the intensity parameters DC and AC are determined therefrom.

These parameters can then be used in order—for example by one of the known methods explained in the introduction—to determine a desired investigation result. The phase shift can thus be used, in an FD spectroscopic method for example, as a measure of the length of the optical path of the light between irradiation site and detection site. Particular preference is given to the use of the measuring method according to the invention in the method described in PCT/DE 94/01290 to determine glucose concentration.

The invention can also be used in the context of the imaging process mentioned earlier. In both of these processes the measuring method according to the invention replaces the known heterodyne process and produces comparable accuracy with a reduced outlay on measuring equipment.

The measuring system requirements of the method according to the invention can be compared with those of the heterodyne measurement procedure as follows. With the heterodyne system a constant modulation with a frequency of 100 MHz at a propagation speed of c/10 produces a wavelength of 300 mm. A measurement distance of 10 mm is consequently equivalent to a phase shift of 12 degrees (10/300×360). If, with the method according to the invention, we adopt the assumptions of the numerical example discussed earlier, the differential frequency of 30 Hz is also equivalent to a phase difference of 12 degrees between beginning and end of the frequency chirp. Assuming that the scatter behaviour of the biological matrix is to be investigated and that the change (caused in particular by a change in glucose concentration) in the mean free path length is 1% (for two different glucose concentrations), a resolution of the measurement of the phase angle of 0.1 degree is required for both methods.

Determination of the parameters, especially the phase difference P of the detected light in relation to the corresponding parameter of the irradiated light, naturally presupposes that information on the phase relation and intensity of the primary light irradiated by the light emitter 10 into the matrix 14 is delivered to the measurement and evaluation unit 30. This is the case in the embodiment according to FIG. 3. A similar supplement can be used in the embodiment according to FIG. 2.

The embodiment represented in FIG. 4 is designed to determine the difference in the above-mentioned parameters between detection sites A and B and A and C. The measured phase difference is thus, for example, a measure of the phase difference between the light detected at these measurement sites. In investigations which are based on the change in the light transit time within the biological matrix (as in PCT/DE 94/01290 for example), such a difference (relating two detection sites) can be just as usefull as a measure of the change in the light transit time as the difference in relation to the irradiation site.

We claim:

1. A method for investigating a light-scattering medium with amplitude modulated light, said method comprising the steps of:
    providing a frequency generator for generating a modulation signal, the modulation signal including frequency chirps wherein a modulation frequency of the modulation signal is tuned from an initial frequency to a final frequency;
    providing a light emitter for irradiating light at an irradiation site on a surface of the light scattering medium, said light emitter being coupled to said frequency generator;
    providing a first signal mixer, said first signal mixer receiving and mixing signals from two signal paths;
    providing two detectors for detecting light along said two signal paths, with one of said two detectors on each of said two signal paths, said two detectors arranged to detect light emerging from the light Scattering medium at two detection sites located at differing measuring distances from the irradiation site, wherein first and second light paths between the irradiation sites and each of the two detection sites on the surface of the light scattering medium have different mean optical path lengths, said two detectors each providing an output signal;
    generating the modulation signal with said frequency generator;
    modulating an amplitude of light emitted from said light emitter with said modulation signal;
    irradiating light from said light emitter into the light-scattering medium at the irradiation site
    detecting light with the two detectors, whereby light travelling from the irradiation site along the two light paths to each of the two detectors have different transit times, and wherein the output signals of the two detectors differ by a differential frequency which depends upon the rate of change of the frequency chirps and a difference between the signal transit times corresponding to the different path lengths;
    applying the output signals of the two detectors to the first signal mixer; and
    determining information regarding the light-scattering medium based upon an output of the first signal mixer.

2. A method for investigating a light-scattering medium as recited in claim 1, wherein said step of irradiating light comprises irradiating light into a biological matrix as the light-scattering medium.

3. A method as recited in claim 1, further comprising the steps of:
    providing a third detector for detecting light along a third signal path, the third detector being arranged to detect light emerging from the light scattering medium at a third detection site located at a distance from the irradiation site which differs from the measurement distances of the first and second detection sites on the surface of the light scattering medium, wherein a third light path between the irradiation site and the third detection site has a different mean optical path length from the mean optical path length of the first and second light paths, said third detector providing an output signal;
    detecting light with the third detector wherein light travelling from the irradiation site along the third light path to the third detector has a different transit time from the transit times of the first and second light paths, and wherein the output signal of the third detector differs from the output signals of the first and second detectors by a differential frequency which depends upon the rate of change of the frequency chirps and the difference between the signal transit times corresponding to the different path lengths;
    providing a second signal mixer;
    applying the output signal of the third detector and the output signal of one of the first and second detector to the second signal mixer; and
    determining information regarding the light scattering medium based upon an output of the first and second signal mixers.

4. A method as recited in claim 1, further comprising a step of delaying the modulation signal by a signal delay means on one of the two signal paths for increasing the differential frequency to a value within a predetermined frequency range.

5. A method according to claim 4, wherein said step of irradiating light includes setting the differential frequency to be between 1 kHz and 30 kHz.

6. A method according to claim 1, further comprising the steps of providing a band pass filter coupled to an output of the first signal mixer, wherein a central frequency of the band pass filter corresponds to the differential frequency; and filtering an output signal of the signal mixer through said band pass filter.

7. A method according to claim 1, wherein said step of irradiating light includes irradiating the light into a biological matrix as the scattering medium, and wherein the frequency chirp in the modulation signal is set to a lowest frequency of 50 MHz and a highest frequency of 1000 MHz.

8. A method according to claim 1, wherein said step of irradiating light includes setting a band width of the frequency chirp to be between 10 MHz and 300 MHz.

9. A method according to claim 1, further comprising the steps of determining a change of the differential frequency caused by changes of a mean light path length in the two light paths, and determining information on the light-scattering medium based upon the change of the differential frequency.

10. A method according to claim 1, wherein a change in phase of the light caused by a change in a mean light path length of at least the first light path is determined, and wherein information on the scattering medium is derived from the determined change in phase.

11. A method according to claim 1, said method further including the steps of determining an intensity parameter of the amplitude-modulated light and determining information on the light-scattering medium based upon the determined intensity parameter.

12. An apparatus for investigating a light-scattering medium with amplitude modulated light, said apparatus comprising:

frequency generator means for generating a modulation signal, the modulation signal including frequency chirps wherein a modulation frequency of the modulation signal is tuned from an initial frequency to a final frequency;

light emitting means coupled to said frequency generator means, said light emitting means for irradiating light at an irradiation site on a surface of the light scattering medium;

signal mixing means for receiving and mixing signals from two signal paths;

detecting means for detecting light along said two signal paths, said detecting means comprising one detector on each of said two signal paths, each detector being arranged to detect light emerging from the light scattering medium at a detection site located at a differing measuring distance from the irradiating site, wherein the two light paths between the irradiation site and each of the detection sites have different mean optical path lengths, each detector providing an output signal;

wherein light travelling from said light emitting means at the irradiation site is detected by the detecting means, and the output signals of the detectors are received by said signal mixing means, wherein input signals to the signal mixing means differ by a differential frequency, and wherein information regarding the light-scattering medium is determined based upon an output of the signal mixing means.

13. An apparatus according to claim 12, wherein said light-scattering medium comprises a biological matrix.

14. An apparatus according to claim 12, wherein said signal mixing means comprises a first signal mixer for mixing and receiving signals from said two signal paths, said apparatus further comprising:

a third detector for detecting light along a third signal path, said third detector being arranged to detect light emerging from the light scattering medium at a third detection site located at a distance from the irradiation site which differs from the measurement distances of the first and second detection sites on the surface of the light scattering medium, wherein the third light path between the irradiation site and the detection site has a different mean optical path length from the mean optical path length of the first and second light paths, said third detector providing an output signal;

a second signal mixer for receiving and mixing signals from the third detector and one of the first and second detectors, wherein light travelling from the irradiation site along the third light path to the third detector is detected, and has a different transit time from the transit times of the first and second light paths, the output signal of the third detector differing from the output signals of the first and second detectors by a differential frequency which depend upon the rate of change of the frequency chirps and the difference between the signal transit times corresponding to the different path lengths, and wherein information regarding the light scattering medium is determined based upon an output of the first and second signal mixers.

15. An apparatus according to claim 12, further comprising a delaying means for delaying the modulation signals on one of the two signal paths for increasing the differential frequency to a value within a predetermined frequency range.

16. An apparatus according to claim 12, said apparatus further comprising a band pass filter coupled to an output of the signal mixing means, said band pass filter for filtering an output signal of the signal mixing means such that a central frequency of the band pass filter corresponds to the differential frequency.

17. An apparatus according to claim 12, wherein changes in phase of the amplitude-modulated light caused by changes in a mean light path over at least the first light path correspond to information regarding the scattering medium.

* * * * *